(12) United States Patent
Couderc et al.

(10) Patent No.: US 7,463,921 B2
(45) Date of Patent: Dec. 9, 2008

(54) METHOD AND SYSTEM FOR ANALYZING AN ELECTROCARDIOGRAPHIC SIGNAL

(75) Inventors: Jean-Philippe Couderc, Rochester, NY (US); Arthur J. Moss, Rochester, NY (US); Wojciech Zareba, Rochester, NY (US)

(73) Assignee: University of Rochester, Rochester, NY (US)

( * ) Notice: Subject to any disclaimer, the term of this patent is extended or adjusted under 35 U.S.C. 154(b) by 673 days.

(21) Appl. No.: 10/217,883

(22) Filed: Aug. 13, 2002

(65) Prior Publication Data
US 2003/0050565 A1 Mar. 13, 2003

Related U.S. Application Data

(60) Provisional application No. 60/311,921, filed on Aug. 13, 2001.

(51) Int. Cl.
*A61B 5/0402* (2006.01)
(52) U.S. Cl. ...................................................... 600/509
(58) Field of Classification Search ................ 600/509; 607/120
See application file for complete search history.

(56) References Cited

U.S. PATENT DOCUMENTS

| | | | | |
|---|---|---|---|---|
| 5,306,293 A | * | 4/1994 | Zacouto | 607/17 |
| 5,560,370 A | | 10/1996 | Verrier et al. | |
| 5,827,195 A | * | 10/1998 | Lander | 600/509 |
| 6,847,840 B2 | * | 1/2005 | DePasquale et al. | 600/509 |
| 2002/0151806 A1 | * | 10/2002 | Starobin et al. | 600/509 |
| 2003/0013978 A1 | * | 1/2003 | Schlegel et al. | 600/509 |

OTHER PUBLICATIONS

M. Merri et al., "Electrocardiographic Quantitation of Ventricular Repolarization," *Circulation*, 80:1301-1307 (1989).
W. Zareba et al., "TU Wave Area-Derived Measure of Repolarization Dispersion in the Long QT Syndrome," *Journal Of Electrocardiology*, 30:191-195 (1998).
J. Benhorin et al., "Long QT Syndrome New Electrocardiographic Characteristics," *Circulation*, 82:523-527 (1990).
M. Hodges et al., "The Extended-Length Electrocardiogram (XL-ECG) A New Tool For Predicting Risk of Sudden Cardiac Death," *Journal of Electrocardiology*, 32:55-59 (1999).
A. J. Moss et al., "Sudden Death and the Idiopathic Long Q-T Syndrome," [editorial] *American Journal of Medicine*, 66(1):6-7 (1979).
A. J. Moss et al., "Delayed Repolarization (QT or QTU Prolongation) and Malignant Ventricular Arrhythmias," *Modern Concepts of Cardiovascular Disease*, 51(3):85-90 (1982).

(Continued)

*Primary Examiner*—George R Evanisko
*Assistant Examiner*—Alyssa M Alter
(74) *Attorney, Agent, or Firm*—Heslin Rothenberg Farley & Mesiti P.C.

(57) ABSTRACT

A method for analyzing an ECG signal includes obtaining a measurement of an area based repolarization interval from at least one beat in the electrocardiogram signal and detecting an altered ventricular repolarization based on the obtained measured area based repolarization interval.

39 Claims, 23 Drawing Sheets

OTHER PUBLICATIONS

B. Surawicz, "ST-Segment, T-Wave, and U-Wave Changes During Myocardial Ischemia And After Myocardial Infarction," *Canadian Journal of Cardiology*, Supplement A:71A-84A (1986).

A. J. Moss, "Prolonged QT-Interval Syndromes," [published erratum appears in *JAMA*, 257(4):487 (1987)]. *JAMA*; 256(21):2985-2987 (1986).

W. Shimizu et al., "Sodium Channel Block with Mexiletine Is Effective In Reducing Dispersion of Repolarization And Preventing Torsade Des Pointes in LQT2 and LQT3 Models Of The Long-QT Syndrome," *Cirulation*, 96(6):2038-2047 (1997).

* cited by examiner

RTx% & RR Interval Bins*

| | RR Interval Bins (msec) | | | |
|---|---|---|---|---|
| ... | 601-700 | 701-800 | 801-900 | ... |
| Baseline: | RTx%b±sd | X1 | X2 | |
| Drug: | RTx%d±sd | X3 | X4 | |
| P-value: | 0.nn | 0.nn | 0.nn | |

\* avoids errors in RTx% correction for heart rate

FIG 7

General Table (1017.twe)

| | Average during 24 hours | Average during Day | Average during Night |
|---|---|---|---|
| RR (bpm) | 99 | 108 | 91 |
| X amplitude (mV) | | | |
| Y amplitude (mV) | 0.27778 | 0.21893 | 0.32782 |
| | | | |
| X RT apex (msec) | 235 | 231 | 240 |
| Y RT apex (msec) | | | |
| Z RT apex (msec) | 217 | 203 | 232 |
| X RT offset (msec) | | | |
| Y RT offset (msec) | 298 | 286 | 306 |
| Z RT offset (msec) | | | |
| X T area 25% (msec) | 102 | 93 | 111 |
| Y T area 25% (msec) | | | |
| Z T area 25% (msec) | 89 | 66 | 111 |
| X T area 50% (msec) | | | |
| Y T area 50% (msec) | 137 | 121 | 157 |
| Z T area 50% (msec) | | | |
| X T area 90% (msec) | 278 | 264 | 292 |
| Y T area 90% (msec) | | | |
| Z T area 90% (msec) | 237 | 231 | 241 |
| X T area 97% (msec) | | | |
| Y T area 97% (msec) | 305 | 282 | 329 |
| | | | |

FIG. 14

Hourly Table (1017.twe)

| Time | Heart Rate (BPM) | T-wave Ampl X | T-wave Ampl Y | T-wave Ampl Z |
|---|---|---|---|---|
| 14:00 | 103 | 0.084012 | 0.18963 | 0.1001 |
| 16:00 | 122 | 0.095323 | 0.20489 | 0.12509 |
| 18:00 | 98 | 0.099484 | 0.21387 | 0.11923 |
| 20:00 | 99 | 0.10036 | 0.22249 | 0.12163 |
| 22:00 | 101 | 0.099274 | 0.23153 | 0.12482 |
| 00:00 | 89 | 0.1019 | 0.23955 | 0.12684 |
| 02:00 | 86 | 0.10516 | 0.25072 | 0.1311 |
| 04:00 | 76 | 0.10772 | 0.2616 | 0.13614 |
| 06:00 | 77 | 0.11012 | 0.27523 | 0.14485 |
| 08:00 | 72 | 0.11192 | 0.29008 | 0.15334 |
| 10:00 | 110 | 0.11036 | 0.28595 | 0.15234 |
| 12:00 | 118 | 0.10823 | 0.27781 | 0.14987 |

FIG 15

Hourly Table (1017.twe)

| Time | Heart Rate (BPM) | T-wave Apex X | T-wave Apex Y | T-wave Apex Z |
|---|---|---|---|---|
| 14:00 | 103 | 239 | 219 | 195 |
| 16:00 | 122 | 234 | 201 | 193 |
| 18:00 | 98 | 231 | 205 | 200 |
| 20:00 | 99 | 230 | 209 | 204 |
| 22:00 | 101 | 231 | 213 | 206 |
| 00:00 | 89 | 233 | 216 | 208 |
| 02:00 | 86 | 233 | 218 | 212 |
| 04:00 | 76 | 234 | 221 | 216 |
| 06:00 | 77 | 236 | 223 | 219 |
| 08:00 | 72 | 237 | 226 | 222 |
| 10:00 | 110 | 236 | 224 | 220 |
| 12:00 | 118 | 235 | 221 | 217 |

FIG. 10

Hourly Table (1017.twe)

| Time | Heart Rate (BPM) | T-wave Offset Lead X | T-wave Offset Lead Y | T-wave Offset Lead Z |
|---|---|---|---|---|
| 14:00 | 103 | 369 | 312 | 291 |
| 16:00 | 122 | 321 | 286 | 265 |
| 18:00 | 98 | 321 | 285 | 270 |
| 20:00 | 99 | 325 | 286 | 277 |
| 22:00 | 101 | 336 | 290 | 278 |
| 00:00 | 89 | 331 | 292 | 279 |
| 02:00 | 86 | 328 | 293 | 281 |
| 04:00 | 76 | 328 | 295 | 284 |
| 06:00 | 77 | 327 | 296 | 286 |
| 08:00 | 72 | 327 | 298 | 289 |
| 10:00 | 110 | 325 | 297 | 289 |
| 12:00 | 118 | 323 | 297 | 285 |

FIG. 17

Hourly Table (1017.twe)

| Time | Heart Rate (BPM) | ABRI RT25 Xlead | ABRI RT25 Ylead | ABRI RT25 Zlead |
|---|---|---|---|---|
| 13:00 | | | | |
| 14:00 | 103 | 106 | 96 | 64 |
| 15:00 | | | | |
| 16:00 | 122 | 92 | 66 | 49 |
| 17:00 | | | | |
| 18:00 | 98 | 92 | 78 | 59 |
| 19:00 | | | | |
| 20:00 | 99 | 94 | 85 | 68 |
| 21:00 | | | | |
| 22:00 | 101 | 97 | 92 | 71 |
| 23:00 | | | | |
| 00:00 | 89 | 100 | 93 | 74 |
| 01:00 | | | | |
| 02:00 | 86 | 101 | 97 | 80 |
| 03:00 | | | | |
| 04:00 | 76 | 102 | 102 | 85 |
| 05:00 | | | | |
| 06:00 | 77 | 103 | 105 | 90 |
| 07:00 | | | | |
| 08:00 | 72 | 104 | 108 | 95 |
| 09:00 | | | | |
| 10:00 | 110 | 103 | 105 | 93 |
| 11:00 | | | | |
| 12:00 | 118 | 102 | 101 | 89 |

FIG. 18

Hourly Table (1017.twe)

| Time | Heart Rate (BPM) | ABRI RT50 Xlead | ABRI RT50 Ylead | ABRI RT50 Zlead |
|---|---|---|---|---|
| 14:00 | 103 | 169 | 144 | 112 |
| 16:00 | 122 | 148 | 108 | 93 |
| 18:00 | 98 | 148 | 118 | 104 |
| 20:00 | 99 | 151 | 123 | 112 |
| 22:00 | 101 | 154 | 130 | 116 |
| 00:00 | 89 | 155 | 132 | 118 |
| 02:00 | 86 | 155 | 135 | 122 |
| 04:00 | 76 | 156 | 139 | 127 |
| 06:00 | 77 | 157 | 141 | 131 |
| 08:00 | 72 | 157 | 144 | 134 |
| 10:00 | 110 | 157 | 141 | 133 |
| 12:00 | 118 | 156 | 137 | 129 |

FIG. 19

Hourly Table (1017.twe)

| Time | Heart Rate (BPM) | ABRI RT90 Xlead | ABRI RT90 Ylead | ABRI RT90 Zlead |
|---|---|---|---|---|
| 13:00 | | | | |
| 14:00 | 103 | 283 | 271 | 243 |
| 15:00 | | | | |
| 16:00 | 122 | 257 | 236 | 219 |
| 17:00 | | | | |
| 18:00 | 98 | 262 | 243 | 225 |
| 19:00 | | | | |
| 20:00 | 99 | 266 | 248 | 235 |
| 21:00 | | | | |
| 22:00 | 101 | 270 | 252 | 240 |
| 23:00 | | | | |
| 00:00 | 89 | 271 | 255 | 238 |
| 01:00 | | | | |
| 02:00 | 86 | 274 | 259 | 236 |
| 03:00 | | | | |
| 04:00 | 76 | 277 | 261 | 235 |
| 05:00 | | | | |
| 06:00 | 77 | 280 | 264 | 237 |
| 07:00 | | | | |
| 08:00 | 72 | 282 | 266 | 238 |
| 09:00 | | | | |
| 10:00 | 110 | 280 | 263 | 238 |
| 11:00 | | | | |
| 12:00 | 118 | 278 | 260 | 237 |

FIG. 20

Hourly Table (1017.twe)

| Time | Heart Rate (BPM) | ABRI RT97 Xlead | ABRI RT97 Ylead | ABRI RT97 Zlead |
|---|---|---|---|---|
| 14:00 | 103 | 306 | 304 | 297 |
| 16:00 | 122 | 275 | 269 | 264 |
| 18:00 | 98 | 283 | 279 | 274 |
| 20:00 | 99 | 288 | 284 | 280 |
| 22:00 | 101 | 292 | 288 | 285 |
| 00:00 | 89 | 294 | 291 | 285 |
| 02:00 | 86 | 299 | 296 | 288 |
| 04:00 | 76 | 305 | 302 | 291 |
| 06:00 | 77 | 311 | 307 | 295 |
| 08:00 | 72 | 315 | 312 | 299 |
| 10:00 | 110 | 313 | 309 | 297 |
| 12:00 | 118 | 310 | 305 | 294 |

FIG. 21

METHOD AND SYSTEM FOR ANALYZING AN ELECTROCARDIOGRAPHIC SIGNAL

This application claims the benefit of U.S. Provisional Patent Application Ser. No. 60/311,921 filed Aug. 13, 2001 which is hereby incorporated by reference in its entirety.

FIELD OF THE INVENTION

The present invention is directed to a method and system for the quantification of repolarization changes when measured in a dynamic electrocardiogram ("ECG") signal.

BACKGROUND OF THE INVENTION

An ECG signal represents changes in electrical potential produced by contractions of the heart recorded from the surface of the body. An example of an ECG signal is illustrated in FIG. 1. Each P-QRS-T complex reflects the electrical depolarization and repolarization components of the heart beat. The cardiac beat comprises three major waves identified as: the P wave representing the depolarization of the auricles, the QRS complex generated by the depolarization of both right and left ventricles, and the T-wave which represents the repolarization of the ventricles. The T wave also includes an apex, $T_{apex}$, and an endpoint, $T_{offset}$. The repolarization of the auricles is hidden in the QRS complex. The RR intervals are defined by the interval between two consecutive R peaks in successive beats. The RR interval is a direct measurement of the heart rate.

In an ECG signal, a modification of the T wave morphology can be observed when certain pharmaceutical agents are taken and also with certain types of cardiac disorders. In particular, it is known that prolongation of the QT interval in an ECG signal is clearly associated with an increased risk for ventricular arrhythmias and sudden cardiac death. Accordingly, prior systems have been developed to monitor the QT interval in ECG signals to detect potential heart problems.

Although these prior systems work, they have problems in accurately identifying the endpoint of the T wave when the endpoint of the T wave gradually approaches the baseline, when a U wave is present, or when the shape of T wave is biphasic. If the apex or the endpoint of the T wave are not accurately identified, the accuracy and robustness of repolarization analysis, i.e. analysis of the QT interval, especially with dynamic ECG signals, such as those obtained by exercise ECG testing, is compromised.

SUMMARY OF THE INVENTION

A method and a computer readable medium with programmed instructions for analyzing an ECG signal in accordance with an embodiment of the present invention includes obtaining a measurement of an area based repolarization interval from at least one beat in the electrocardiogram signal and detecting an altered ventricular repolarization based on the obtained measured area based repolarization interval.

A system for analyzing an ECG signal in accordance with an embodiment of the present invention includes a measurement system and a detection system. The measurement system obtains a measurement of an area based repolarization interval from at least one beat in the electrocardiogram signal. The detection system detects an altered ventricular repolarization based on the obtained measured area based repolarization interval.

A method and a computer readable medium with programmed instructions for analyzing an effect of a pharmacological agent on an electrocardiogram signal in accordance with an embodiment of the present invention includes obtaining a first measurement of an area based repolarization interval from at least one beat in the electrocardiogram signal. The pharmacological agent is administered. A second measurement of an area based repolarization interval from at least one beat in the electrocardiogram signal is obtained from at least one of a first period during which the pharmacological agent is in effect and a second period after the pharmacological agent is no longer in effect. An altered ventricular repolarization is detected based on the first and second measurements.

A system for analyzing an effect of a pharmacological agent on an electrocardiogram signal in accordance with an embodiment of the present invention includes a measurement system and a detection system. The measurement system obtains a first measurement of an area based repolarization interval from at least one beat in the electrocardiogram signal before administering the pharmacological agent. The measurement system also obtains a second measurement of an area based repolarization interval from at least one beat in the electrocardiogram signal from at least one of a first period during which the pharmacological agent is in effect and a second period after the pharmacological agent is no longer in effect. The detection system detects an altered ventricular repolarization based on the first and second measurements.

The present invention provides an effective non-invasive method for dynamic quantification of ventricular repolarization. The present invention's comprehensive evaluation of ventricular repolarization provides enhanced utility: in the clinical diagnosis of acquired and inherited repolarization disorders; in the evaluation of new chemical entities for pharmaceutical companies during drug development and during post-marketing surveillance of approved drugs that can adversely affect ventricular repolarization; and in the clinical identification of patients with potentially life-threatening ventricular repolarization disorders, such as those after myocardial infarction.

BRIEF DESCRIPTION OF THE DRAWINGS

FIG. 7 is a table of RTx % and RR interval bins;

FIG. 14 is a table of averages for 24 hours, during the day and at night for: beats per minute (BPM); X, Y, and Z amplitudes; X RT apex, Y RT apex, and Z RT apex; X RT offset, Y RT offset, and Z RT offset; XT 25% area, YT 25% area and ZT 25% area; XT 50% area, YT 50% area and ZT 50%; area XT 90% area, YT 90% area and ZT 90%; and area XT 97% area, YT 97% area and ZT 97% area;

FIG. 15 is an hourly table of heart rate (BPM), T wave ampl X, T wave ampl Y, and T wave ampl Z;

FIG. 16 is an hourly table of heart rate (BPM), T wave apex X, T wave apex Y, and T wave apex Z;

FIG. 17 is an hourly table of heart rate (BPM), T wave offset lead X, T wave offset lead Y, and T wave offset lead Z;

FIG. 18 is an hourly table of heart rate (BPM), ABRI RT25 X-lead, ABRI RT25 Y-lead, and ABRI RT25 Z-lead;

FIG. 19 is an hourly table of heart rate (BPM), ABRI RT50 X-lead, ABRI RT50 Y-lead, and ABRI RT50 Z-lead;

FIG. 20 is an hourly table of heart rate (BPM), ABRI RT90 X-lead, ABRI RT90 Y-lead, and ABRI RT90 Z-lead;

FIG. 21 is an hourly table of heart rate (BPM), ABRI RT97 X-lead, ABRI RT97 Y-lead, and ABRI RT97 Z-lead;

DETAILED DESCRIPTION

Figure 1:
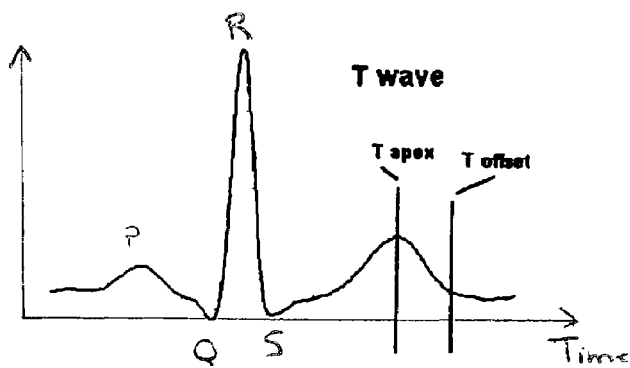
FIG. 1 is a diagram of a beat in an ECG signal where two vertical lines mark the apex and the offset of the T wave used to measure QT intervals.
Figure 2:
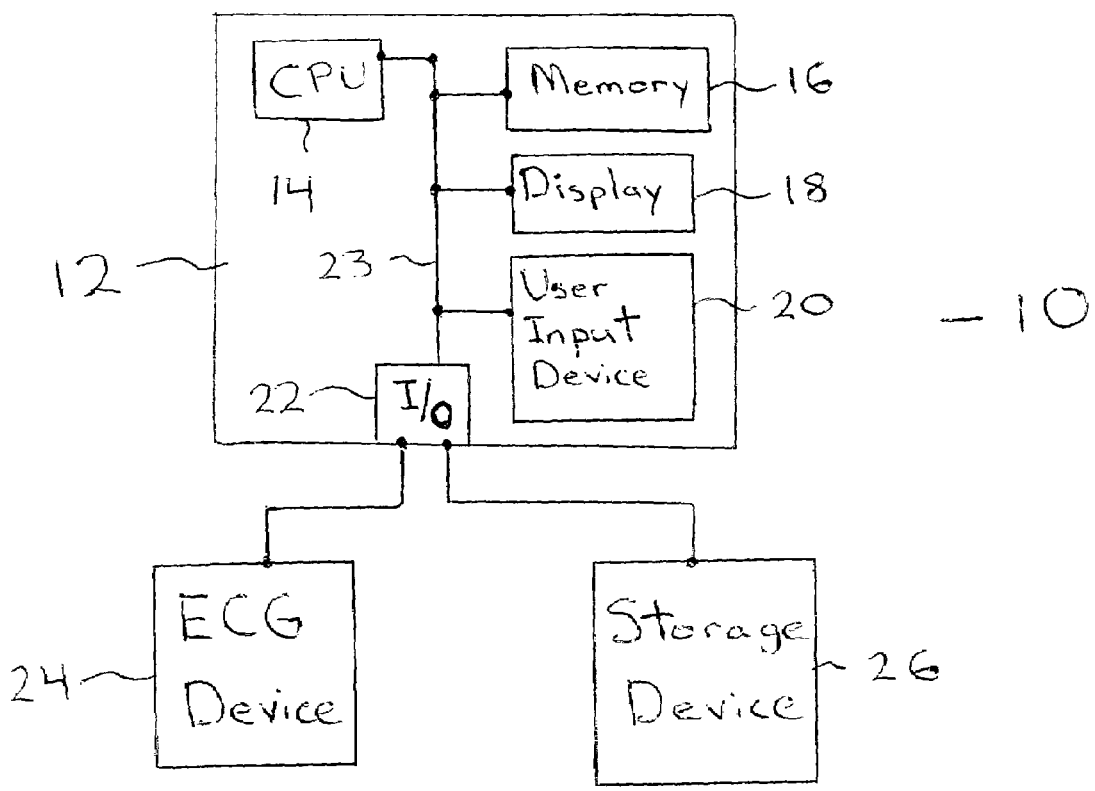
FIG. 2 is a block diagram of a quantification system in accordance with one embodiment of the present invention.
Figure 4:
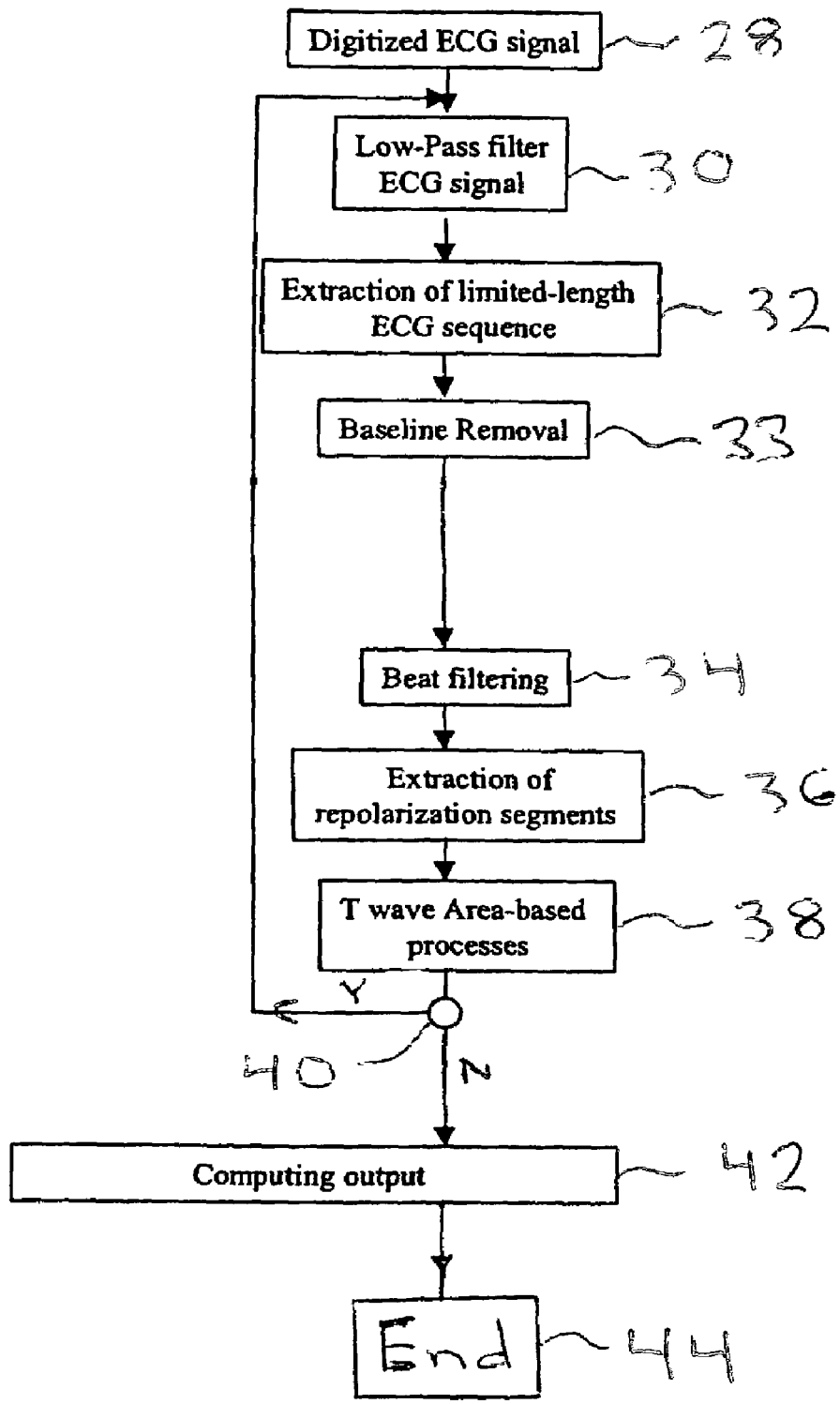
FIG. 4 is a flow chart of a method for analyzing an ECG signal in accordance with another embodiment of the present invention.

A system 10 and method for analyzing an ECG signal in accordance with one embodiment of the present invention are illustrated in FIGS. 2 and 4. In this particular embodiment, the system 10 includes a quantification system 12 coupled to an ECG device 24 and a storage device 26. The method includes filtering and then extracting a portion of the filtered ECG signal, substantially removing any baseline from the extracted portion of the ECG signal, obtaining a measurement of at least one area based repolarization interval in the extracted portion, and then detecting any altered ventricular repolarization based on the measured area based repolarization interval. The present invention provides a number of advantages including providing an effective non-invasive method for dynamic quantification of ventricular repolarization.

Referring to FIG. 2, the quantification system 12 has a central processing unit ("CPU") or processor 14, a memory 16, an input/output interface 22, a display 18, and a user input device 20 which are coupled together by a bus system 23 or other link, although the quantification system 12 may comprise other types of components, other numbers of the components, and other combinations of the components. The processor 14 executes a program of stored instructions for at least a portion of the method for analyzing an ECG signal in accordance with one embodiment of the present invention as described herein. In this particular embodiment, the preprocessing and processing steps are carried out by quantification system 12, although other types and combinations of systems and/or devices can be used to execute the preprocessing and processing steps.

Memory 16 comprises a random access memory (RAM) and a read only memory (ROM), although other types and combinations of memory storage devices can be used, such as a floppy disk, hard disk, CD ROM, or other computer readable medium which is read from and/or written to by a magnetic, optical, or other reading and/or writing system that is coupled to the processor 14. Although in his particular embodiment, the method in accordance with one embodiment of the present invention is stored as programmed instructions in memory 16 in the quantification system 12 for execution by the processor 14, some or all of the programmed instructions could be stored elsewhere.

The display 18 enables an operator to observe information, such as the ECG reading for a patient. In this particular embodiment, the display 18 is a cathode ray tube device, although other types of displays can be used, such as a printer.

The user input device 20 enables an operator to generate and transmit signals or commands to the processor, such as a request to obtain or retrieve ECG signals for a particular patient for processing. In this particular embodiment, the user input device 20 is a keyboard, although other types of user input devices can be used, such as a computer mouse.

The input/output interface 22 is used to operatively couple the quantification system 12 to the ECG device 24 and the storage device 26, although quantification system 12 can be coupled via input/output interface to other systems and/or devices.

The ECG device 24 records one or more ECG signals from one or more patients. The ECG device can capture the electrical activity from the heart in a variety of different manners, such as Holter recordings, exercise ECG testing, bedside ECG monitoring, event monitoring, implantable ECG recorders using one or more leads and with a duration that may vary from few minutes to twenty-four hours, even few days. A variety of different types of ECG devices can be used for ECG device 24. The ECG information can be transmitted to the quantification system 12 from the ECG device 24 for processing.

The storage device 26 comprises a RAM, although other types and combinations of memory storage devices can be used, such as a ROM or a floppy disk, hard disk, CD ROM, or other computer readable medium which is read from and/or written to by a magnetic, optical, or other reading and/or writing system. The storage device 26 can store ECG readings for processing by the quantification system 12 and can store the results of any processing.

Figure 3A:
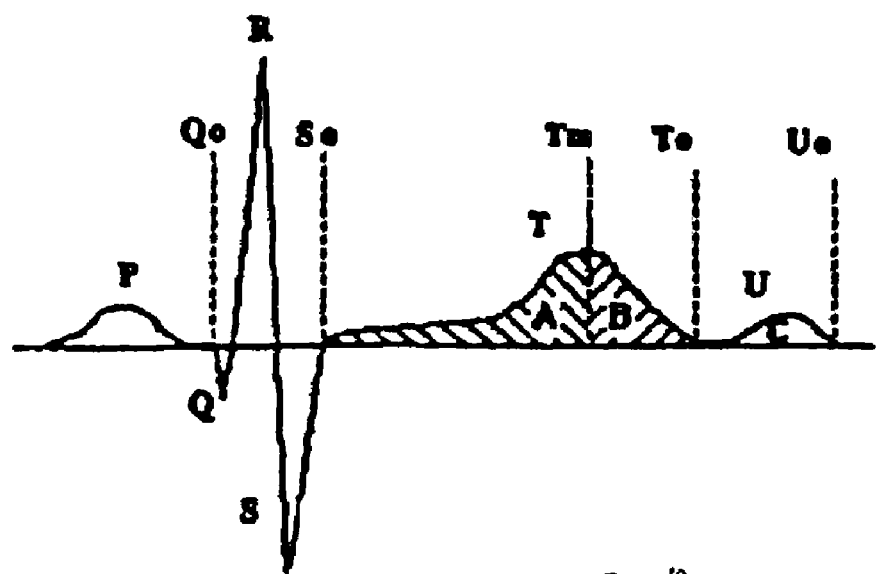
FIG. 3A is a diagram of another ECG signal.

Referring to FIG. 3A, an example of another ECG signal is illustrated. In this particular example, the Q peak is reached at time $Q_0$, the T wave begins at time $S_0$, the T apex is reached at $T_m$, and the endpoint of the T wave is reached at $T_o$.

Figure 3B:
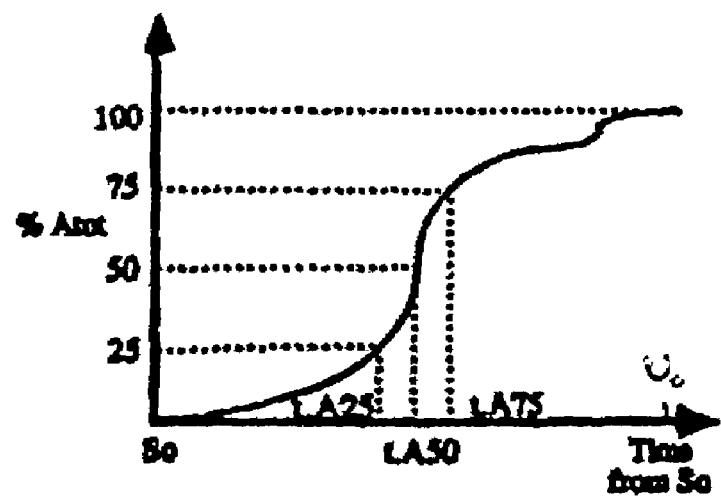
FIG. 3B is a graph of a normalized absolute integral of the repolarization segment of the ECG signal shown in FIG. 3A.

Referring to FIG. 3B, a graph of the measured area under the repolarization interval shown in FIG. 3A with the Y-axis showing the percentage of the total area under the repolarization interval and the X-axis showing time is illustrated. The graph begins at time $S_0$ which again corresponds to the time when the T wave begins and $T_0$ represents the time when substantially 100% of the area under the repolarization area is measured. The times to accumulate 25%, 50%, and 75% of the absolute T-wave area are identified as LA25, LA50, and LA75, respectively. Unlike prior systems, the present invention does not rely upon accurately determining either the T apex, $T_m$, or the endpoint of the T wave, $T_o$. Instead, the present system identifies the end of the T wave when the slope of the repolarization signal is below a given threshold. The present invention quantifies changes in ventricular repolarization based on measurements of the area under the repolarization interval obtained starting at a time $S_0$, which is a first period of time after the R peak is detected.

The morphology of the repolarization T wave in an ECG signal, such as the one shown in FIG. 3A, can be influenced by any factor that alters ion-channel kinetics involved in ventricular repolarization, including inherited diseases, acquired cardiac diseases, metabolic disturbances, and drugs. Since the normal morphology of the ventricular repolarization interval is well known to those of ordinary skill in the art, an altered or abnormal morphology ventricular repolarization interval can be both visually and quantitatively assessed if it is accurately measured. A process for analyzing ventricular repolarization in accordance with the present invention is described below.

Referring to FIGS. 2, 3A, 3B, and 4, a method for analyzing an ECG signal in accordance with one embodiment is described below. Beginning in step 28, the quantification system 12 obtains an ECG signal or signals. The ECG signals can be obtained from a variety of different sources, such as directly from the ECG device 24 or from the storage device 26 which stores previously recorded ECG signals.

In step 30, the ECG signal undergoes low pass-filtering in quantification system 12. The filtering technique used should preserve the initial shape of the T wave. In this particular embodiment, the ECG signal is filtered in the forward direction, the filtered ECG signal is then reversed and run back through the filter again. The result of this filtering operation has precisely zero phase distortion and magnitude modified by the square of the filter's magnitude response.

Figure 5A:
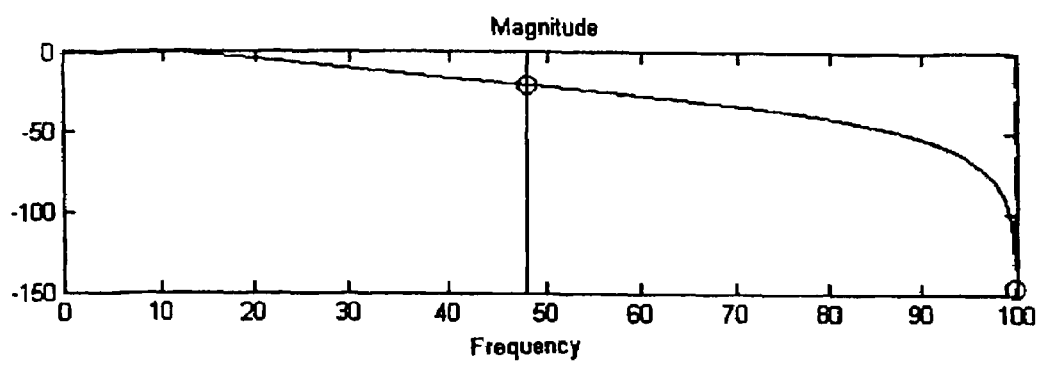
FIGS. 5A-5C are graphs of the magnitude, phase, and zeros and poles of a filter for the quantification system.
Figure 5B:
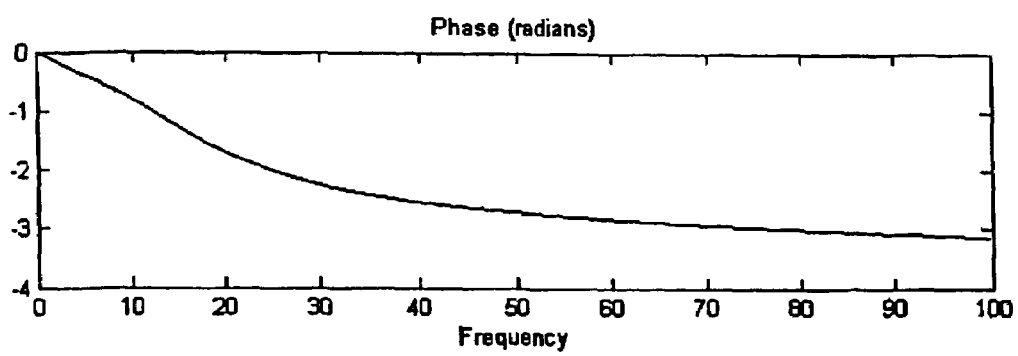
Figure 5C:
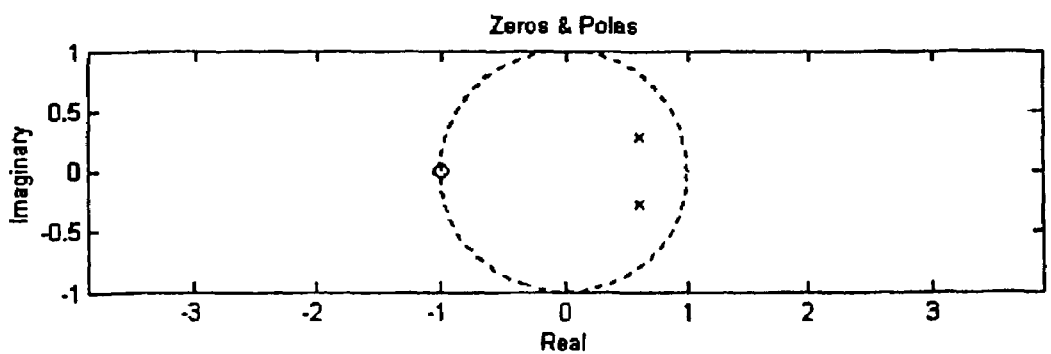

By way of example only, in this particular embodiment a Butterworth filter and a bidirectional filtering technique are used in order to obtain a high quality filtering free of distorted components, although other types of filters and filtering techniques can be used. In this example, a filter of order two with a cutoff frequency at −3 db equal to 18 Hz is used. Graphs of the magnitude, phase (radians) and zeros and poles of this filter used for removing noise components of the ECG signal and reducing morphological changes of area based repolarization interval are illustrated in FIGS. 5A-5C.

Referring back to FIG. 4, in step 32 a portion or limited length sequence of the filtered ECG signal is extracted by the quantification system 12. More specifically, the ECG signal is cut into portions or sequences of consecutive continuous beats by quantification system 12, excluding non-normal beats. In each of these portions, R(k) is the R peak location in the $k^{th}$ beat in each portion and ECG(n) is the $n^{th}$ portion of ECG signal where n represents the number of portions of the ECG signal. Each ECG portion which is analyzed is ECG(n) for n ∈[R(k), R(k+NB)] where NB is the number of beats in each analyzed interval. In this example, a repolarization segment is extracted for each of seventy consecutive beats in the filtered ECG signal.

In step 33, the baseline B(k) of the extracted portion of the ECG signal ECG(n) is substantially removed by the quantification system 12. The baseline removal must be accurate and must avoid adding significant components to the repolarization segment in the ECG signal ECG(n). By way of example only, in this particular embodiment the baseline removal can be obtained based using a Cubic-Spline interpolation of the baseline of the ECG signal ECG(n), although other techniques for removing the baseline can be used. The interpolation used in this particular example is based on the average amplitude value of the samples from a limited squared time window W(n) of 80 ms length located just before the beginning of the QRS complex. B(k) is defined such as: B(k)=ECG(R(k)−16) for a signal at 200 Hz sampling frequency. The signal B(k) is interpolated at a sampling period equal to the sampling period of the ECG. The Cubic Spline interpolation of B(k) is used to insure continuous smoothness up to the second derivative and is less likely to generate erratic oscillations than polynomial interpolation. The interpolated curve, corresponding to the very low components of the ECG signal ECG(n), is subtracted from the ECG signal ECG(n) in order to reduce the effect of respiratory components of the signal. After subtracting the estimated baseline, two beats are removed from the beginning and two beats from the end of the analyzed intervals in the ECG signal ECG(n). In this particular example, two beats are removed from the extremities of the ECG signal with seventy beats resulting in sixty-six beats which are analyzed. This insures elimination of undesirable side effects of the Cubic Spline interpolation that may occur at the beginning and the end of the analyzed portion of the ECG signal ECG(n) which may alter the morphology of T wave;

In step 34, the portion of the ECG signal ECG(n) with the baseline removed is now subjected to beat filtering to remove non-normal beats from the analysis by quantification system 12. No interpolation of the missing beats is necessary since continuity of the measurement on a beat to beat basis is not needed.

In step 36, repolarization segments for each of the beats portion of the ECG signal ECG(n) are extracted by quantification system 12 after the non-normal beats are removed in step 34. More specifically, in one embodiment $ST_k(n)$ segments are extracted from the ECG signal ECG(n) based on two-level criterion: the first step identifies the end of the repolarization wave where the slope (first derivative) of the terminal portion of the repolarization equal or inferior to 0.1 mV. The scanning process is going forward relatively to time. If such criterion is not met because the signal does has such characteristic then: $ST_k(n)=ECG(m)$ for:

$$m \in [R(k)+D, \beta(k+1)-R(k))] \quad (1)$$

By way of example only, at a 200 Hz sampling frequency (SF), D is equal to sixteen in order to have a repolarization segment beginning 100 msec after the R peak of the complex k. β is equal to ⁴⁄₇ for normal range of heart rate (50-100 bpm), but can be manually adjusted for heart rate outside of this range. As previously described, the repolarization interval is defined either by a flat segment at the end of the repolarization segment or as a portion of the RR interval of the currently analyzed beat. All $ST_k(n)$ intervals beginning D/SF (sixteen samples at 200 Hz for 80 msec) after the R peak.

In another embodiment, $ST_k(n)$ segments are extracted from the ECG signal ECG(n) from a starting time $S_0$ for each segment until an endpoint of the T wave is reached at $T_o$ for each segment. The starting time $S_0$ for each segment is established as a first period of time, such as 100 msec after the R peak, although this time can vary as needed. For example, the particular point for starting time $S_0$ can be modified in order to avoid including QRS complex components in the area based measurements when a patient has electrical abnormalities leading to an increased QRS complex duration, such as patient with bundle branch block. In this embodiment, the starting time $S_0$ is set by an operator after analyzing the ECG signal for a particular subject, although the starting time $S_0$ could be established in other manners, such as by an analysis of a characteristic or characteristics of the ECG signal by the quantification system 12. In this embodiment, the endpoint of the T wave $T_o$ for each segment is established when the slope of the T wave goes below a threshold slope which is set in the quantification system 12, although the endpoint of the T wave can be established in other manners. This threshold slope can be changed by the operator. The slope of the T wave portion of the segment is taken by the quantification system 12 by taking a derivative of the T wave portion of that segment, although the quantification system can determine the slope in other manners.

In this embodiment, a median signal $ST_r(n)$ is computed from a set of segments $ST_k(n)$ such as: $ST_r(n)$=median([$ST_3(n), \ldots, ST_{NB-2}(n)$]). The index r identifies the set of NB beats, with the values of r ranging from three to NB−2. For instance, as described earlier the initial portion of the ECG(n) can include seventy beats with two beats removed at each of the extremities of the portion of the ECG signal resulting in sixty-six beats analyzed with each analyzed set being eleven beats, although the size of the analyzed set can vary as needed.

Figure 6A:
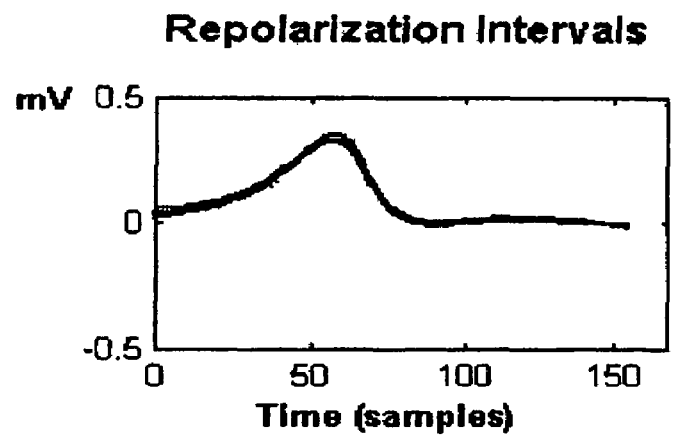
FIG. 6A is a graph of six area based repolarization intervals of median beats which are superimposed.
Figure 6B:
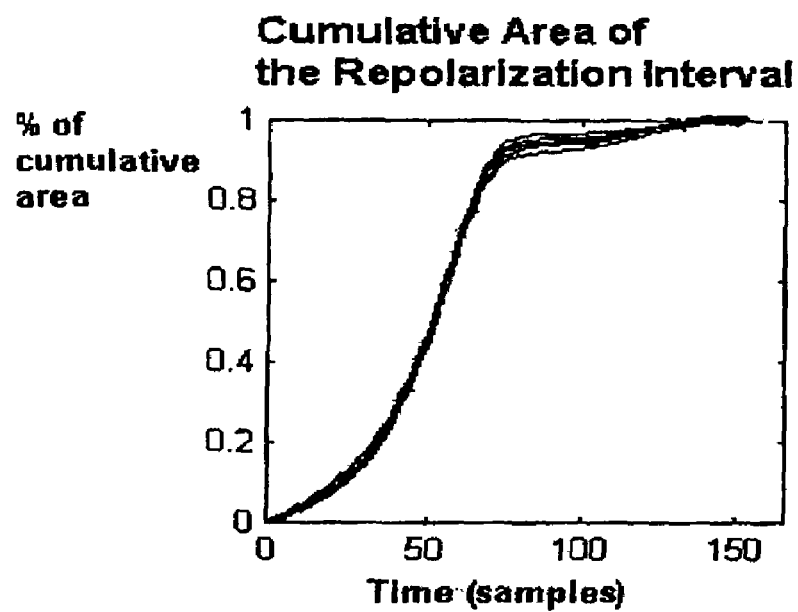
FIG. 6B is a graph of cumulative area of the six area based repolarization intervals shown in FIG. 6A.
Figure 8A:
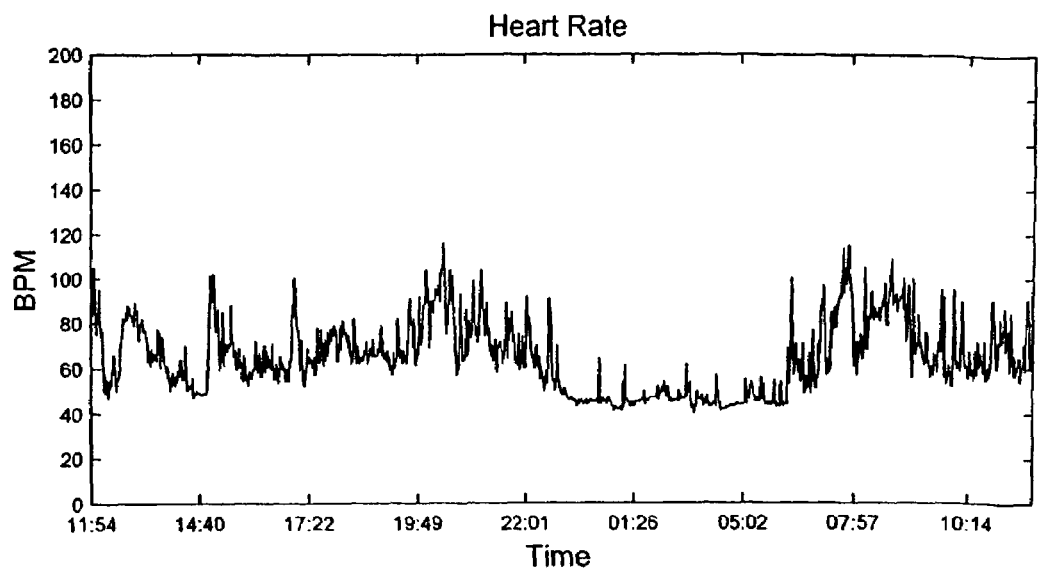
FIG. 8A is a graph of a heart rate of one patient showing beats per minute (BPM) against time.
Figure 8B:
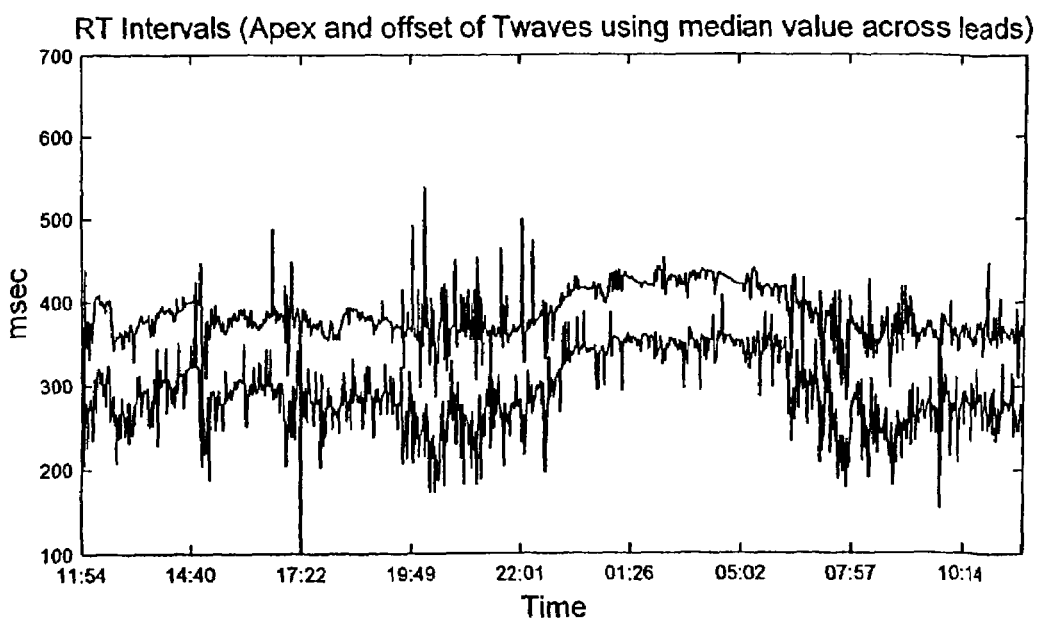
FIG. 8B is a graph of a RT intervals (Apex and offset of T waves using median value across leads) of the one patient.
Figure 9A:
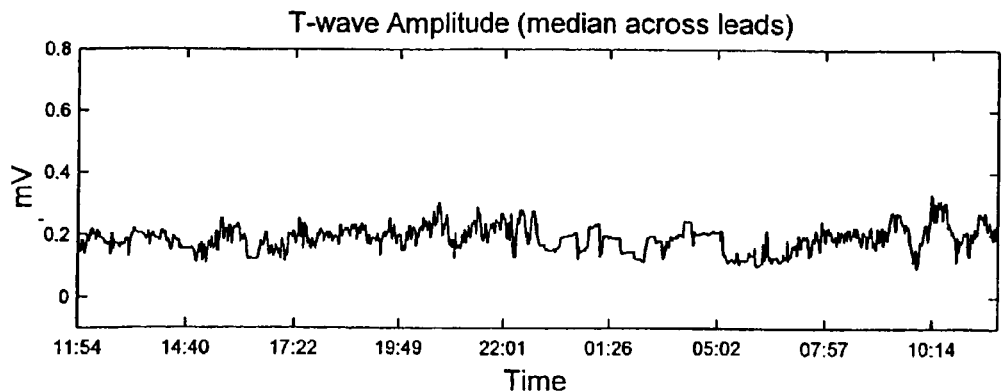
FIGS. 9A-9D are graphs of trends for T-wave amplitude for the median across leads, the X leads, the Y leads, and the Z leads.
Figure 9B:
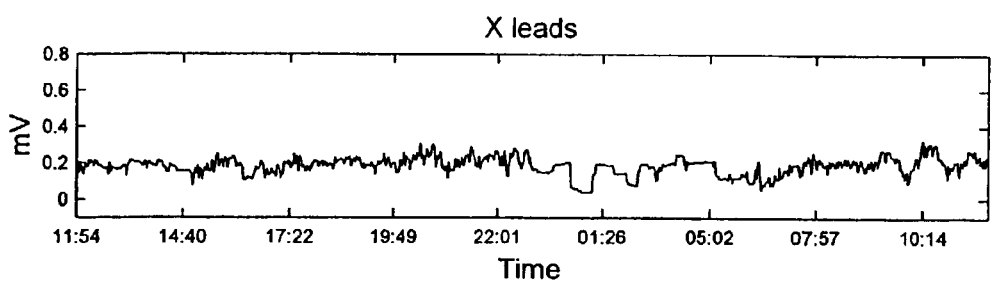
Figure 9C:
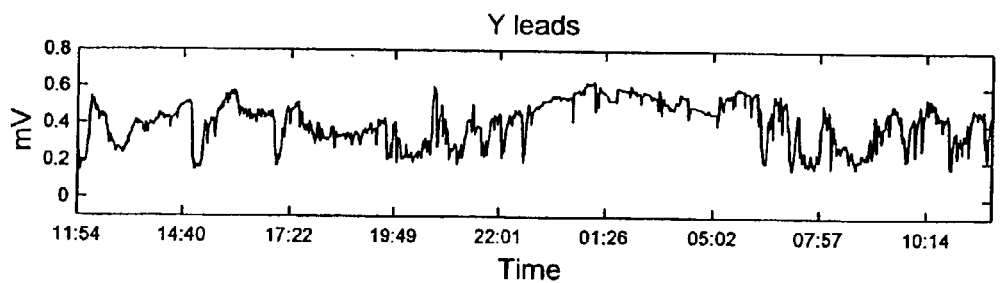
Figure 9D:
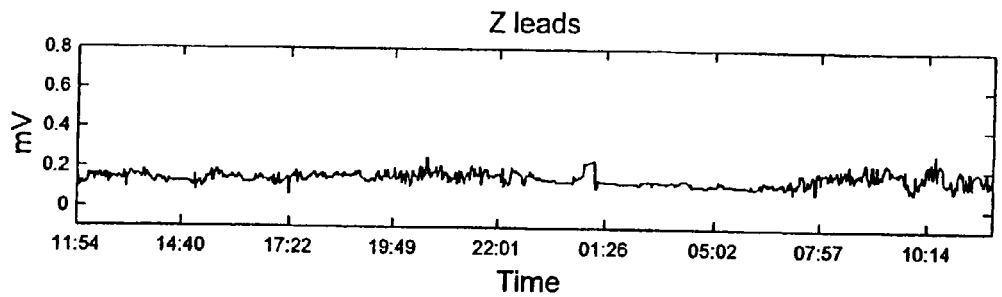
Figure 10A:
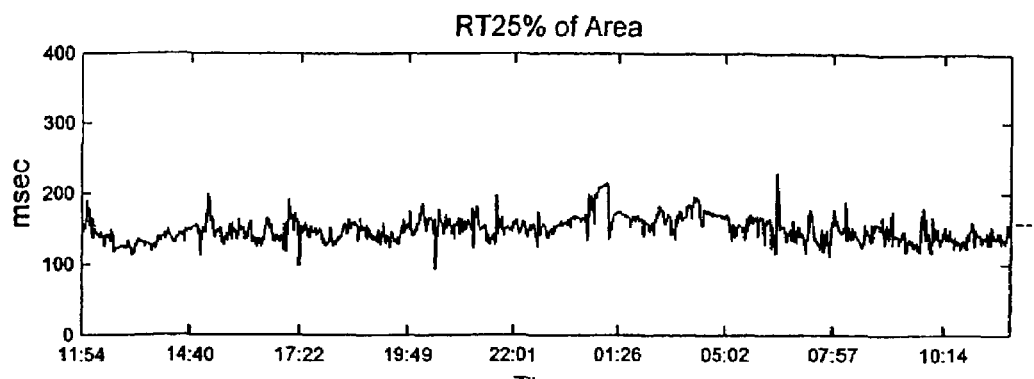
FIGS. 10A-10D are graphs of the trends for area-based measurements for 25% of the area for the median, the X leads, the Y leads, and the Z leads.
Figure 10B:
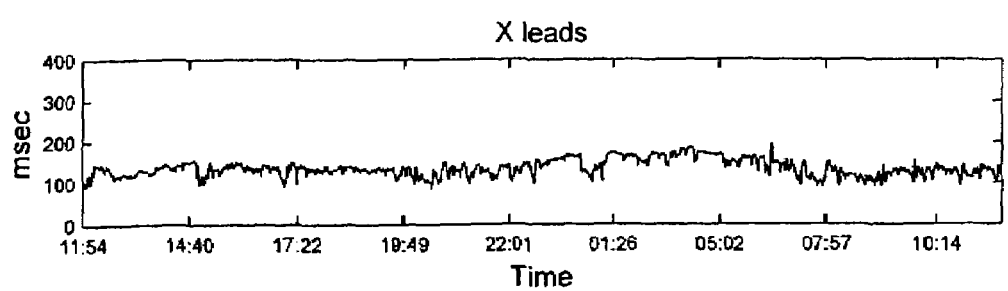
Figure 10C:
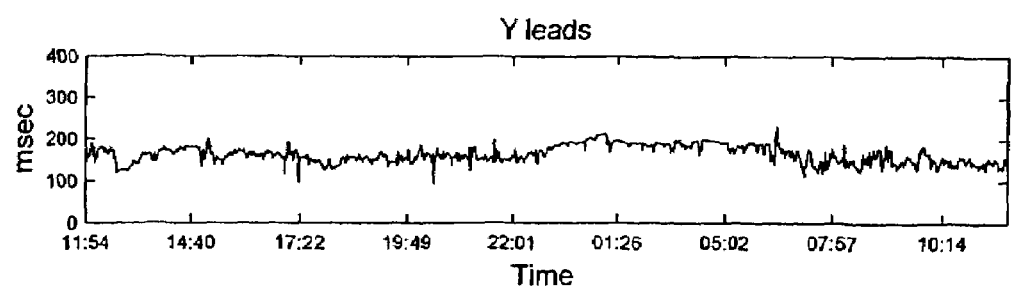
Figure 10D:
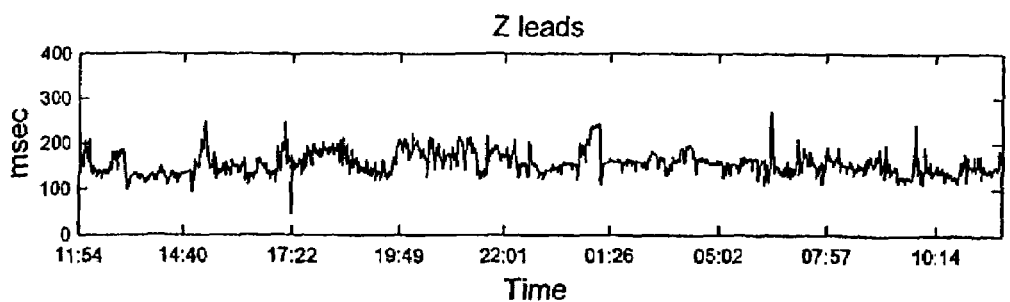
Figure 11A:
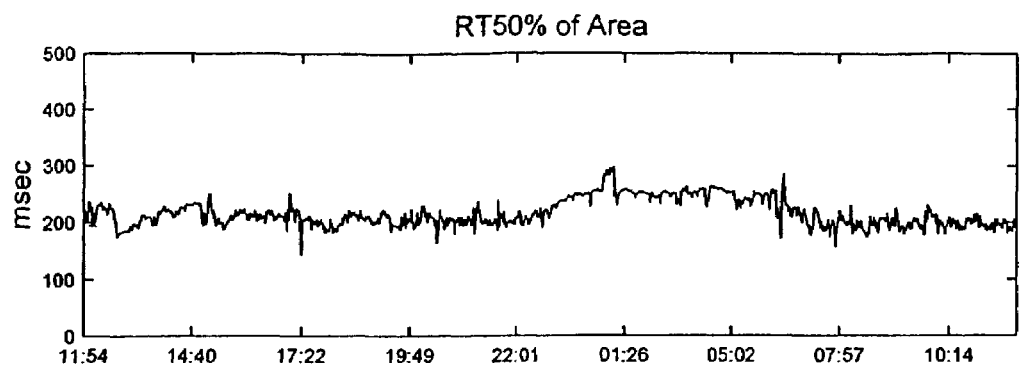
FIGS. 11A-11D are graphs of the trends for area-based measurements for 50% of the area for the median, the X leads, the Y leads, and the Z leads.
Figure 11B:
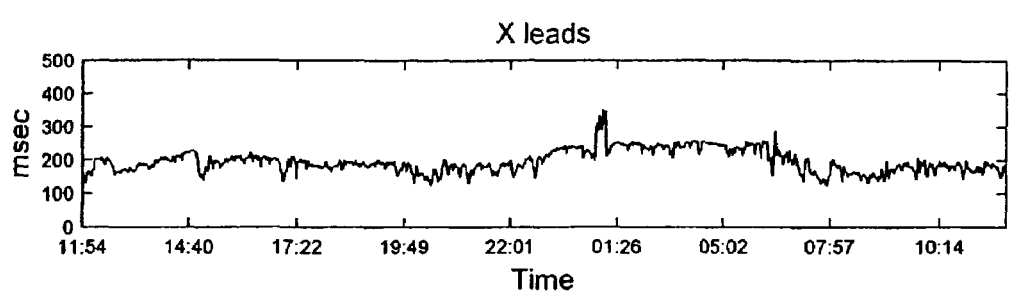
Figure 11C:
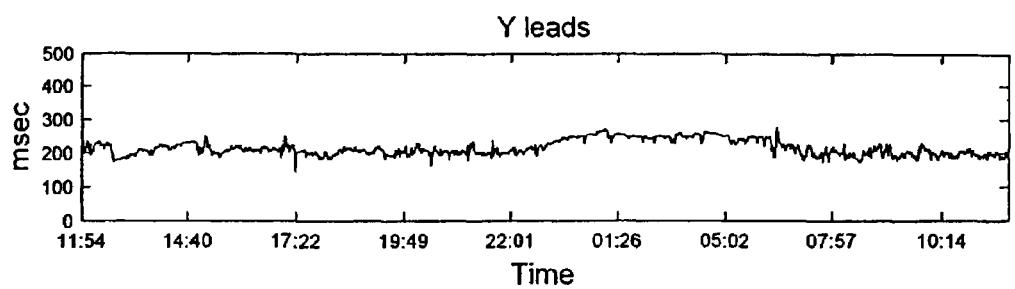
Figure 11D:
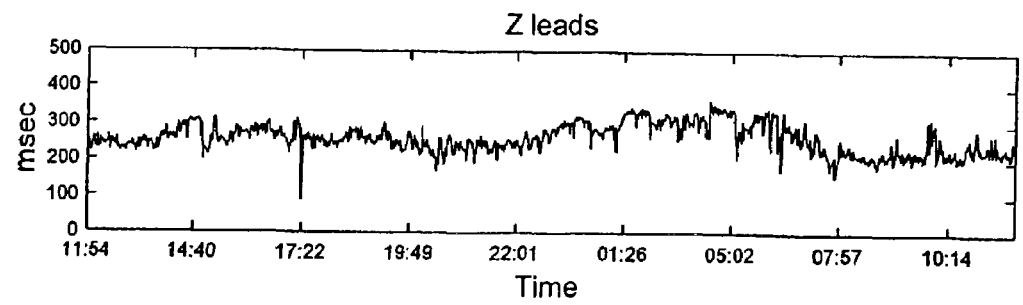
Figure 12A:
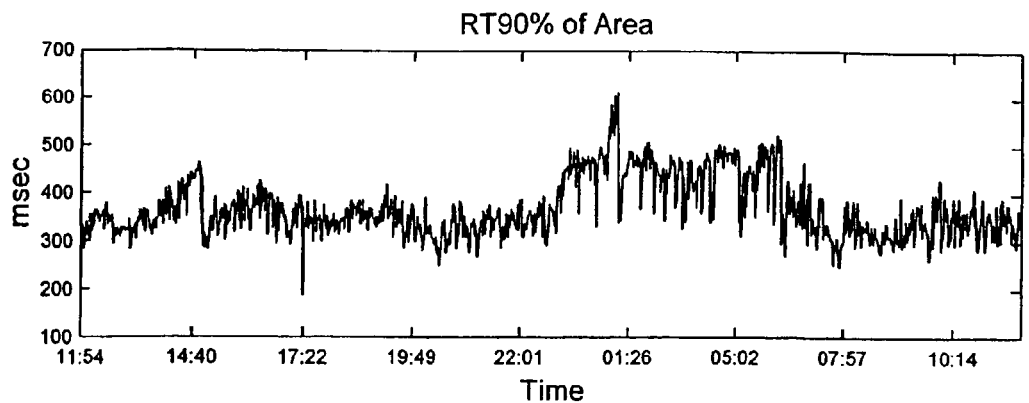
FIGS. 12A-12D are graphs of the trends for area-based measurements for 90% of the area for the median, the X leads, the Y leads, and the Z leads.
Figure 12B:
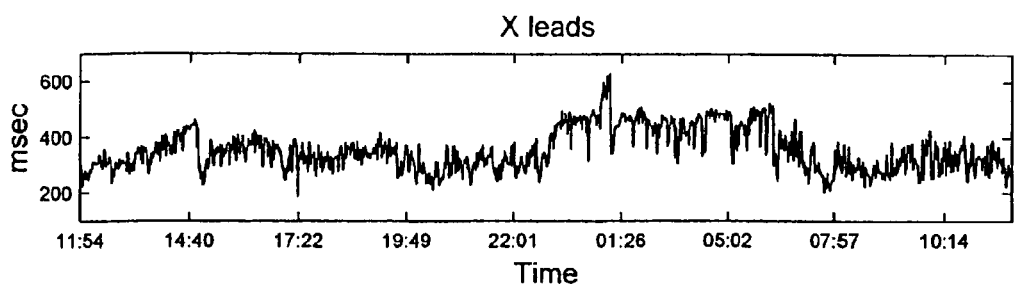
Figure 12C:
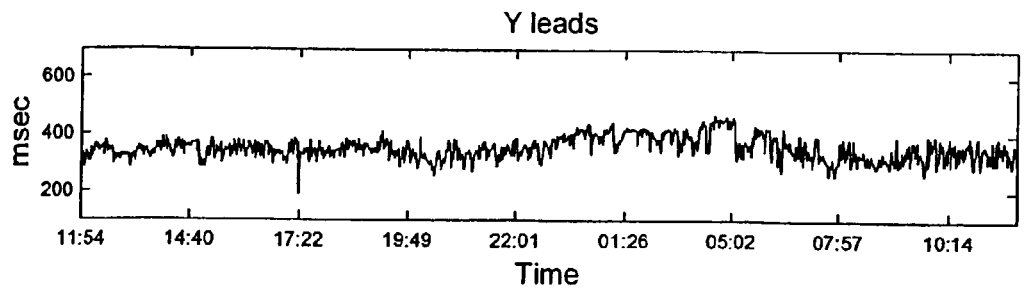
Figure 12D:
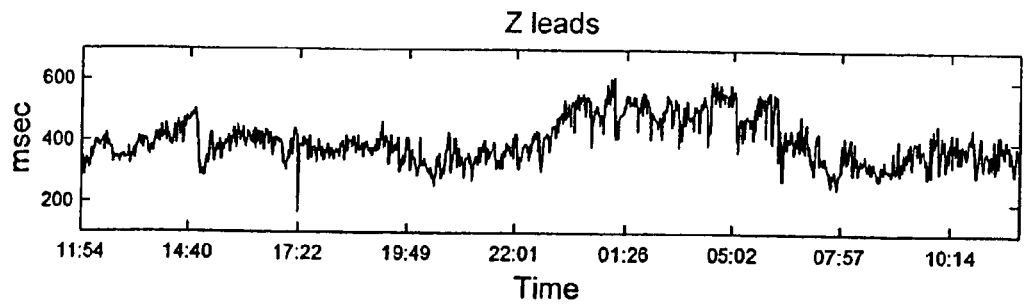
Figure 13A:
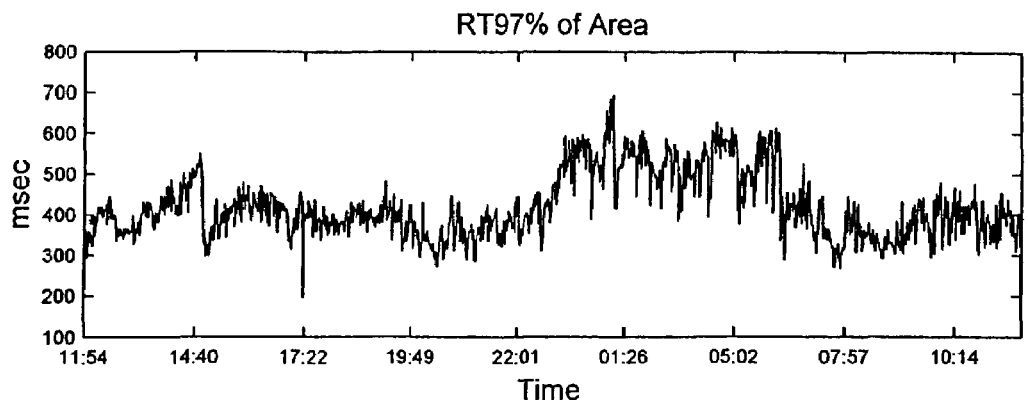
FIGS. 13A-13D are graphs of the trends for area-based measurements for 97% of the area for the median, the X leads, the Y leads, and the Z leads.
Figure 13B:
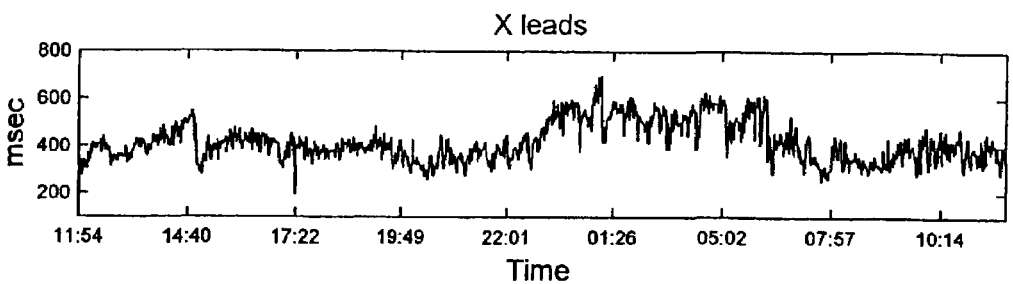
Figure 13C:
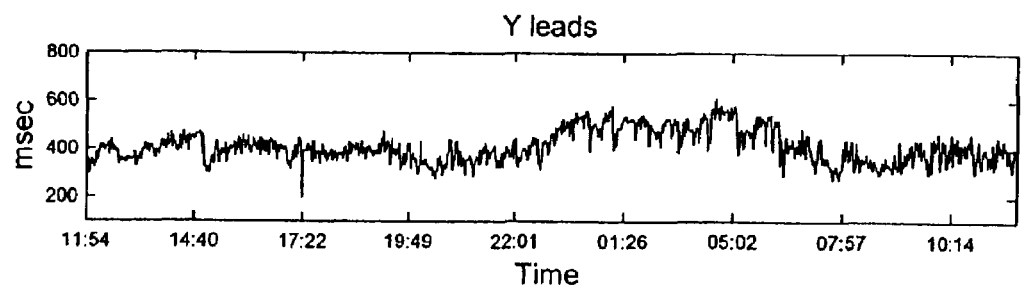
Figure 13D:
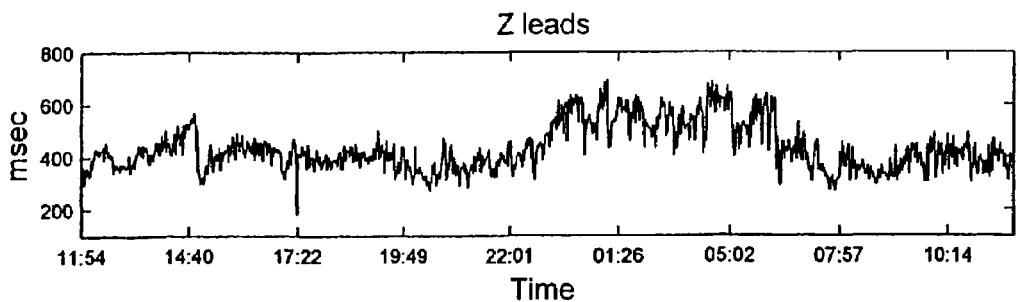
Figure 22A:
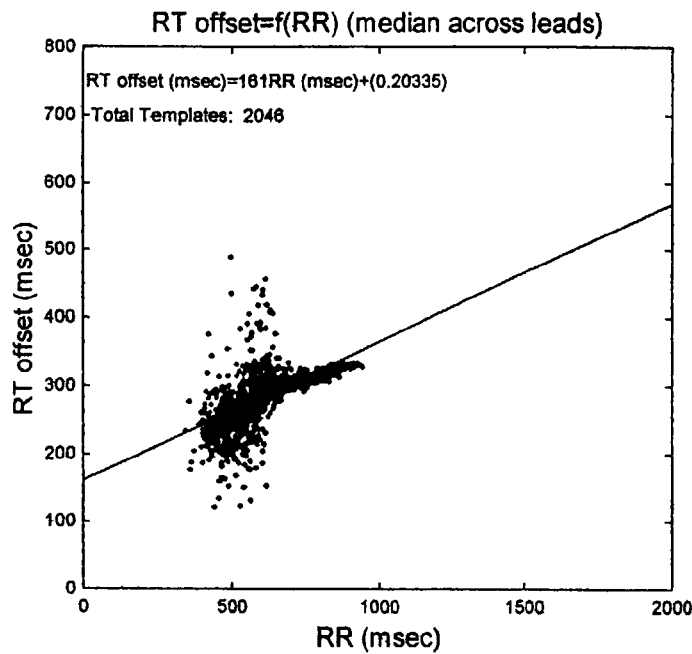
FIGS. 22A-22B are graphs of PointCarre plots over 24-hours of RT offset=f(RR) (median across leads) and RT apex=f(RR) (median across leads)
Figure 22B:
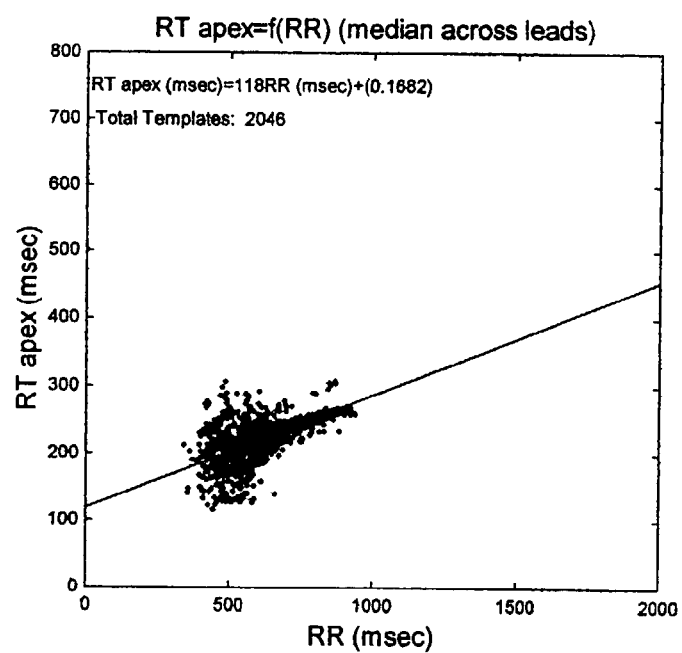
Figure 23A:
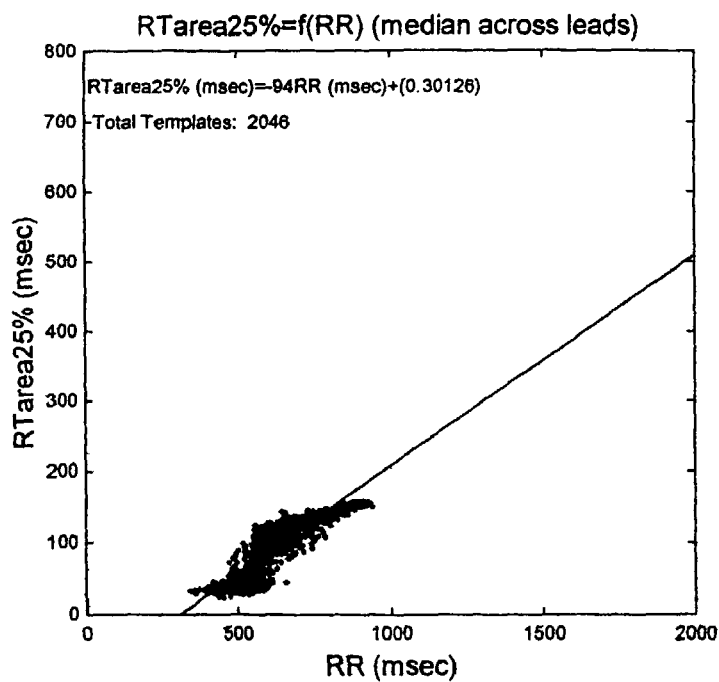
FIGS. 23A-23B are graphs of PointCarre plots over 24-hours of RT area 25%=f(RR) (median across leads) and RT area 50%=f(RR) (median across leads)
Figure 23B:
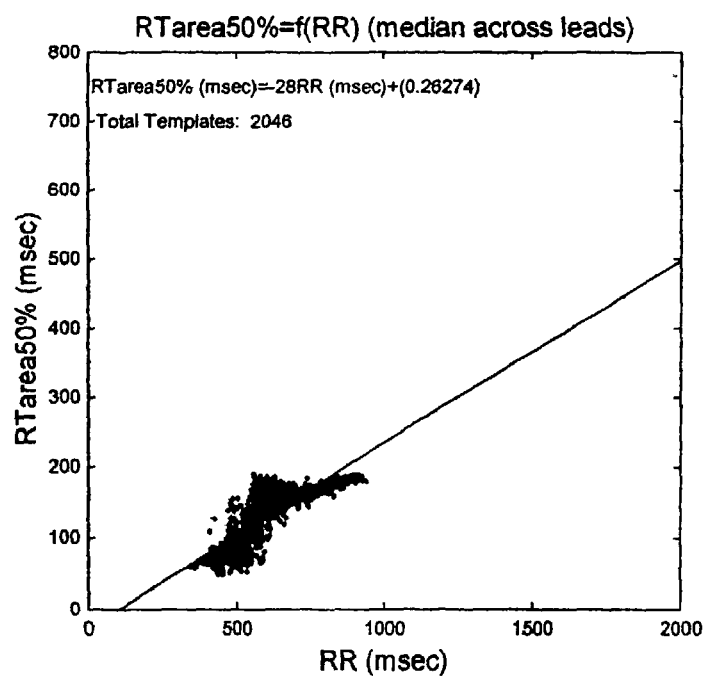
Figure 24A:
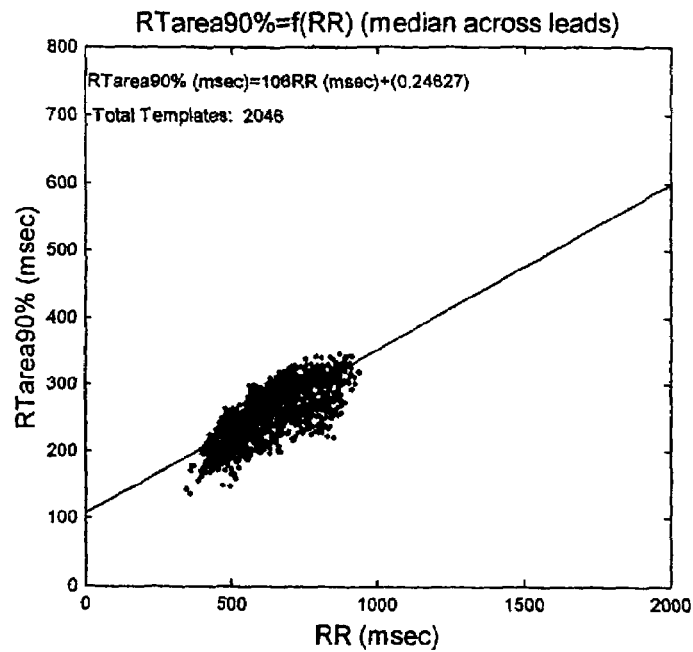
FIGS. 24A-24B are graphs of PointCarre plots over 24-hours of RT area 90%=f(RR) (median across leads) and RT area 97%=f(RR) (median across leads).
Figure 24B:
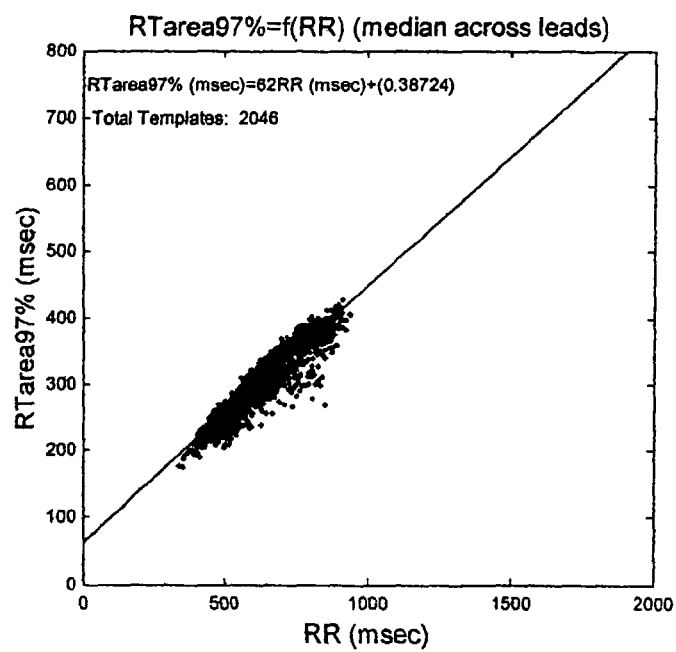

In step 38, in one embodiment an area based repolarization interval for each of the extracted repolarization segments $ST_k(n)$ for the portion of the ECG signal ECG(n) are obtained or measured by the quantification system 12. The area is obtained by the mathematical integration of each of the extracted repolarization segments $ST_k(n)$ by the quantification system 12 from the starting time $S_0$ to various percentages of the ST segment $ST_k(n)$. The time needed to reach different percentages of the total area from the starting time $S_0$ (shown in FIG. 3B) is measured and recorded. In this particular embodiment, the times needed to reach 25%, 50%, 90% and 97% of the area based repolarization interval for each of the extracted repolarization segment $ST_k(n)$ are recorded, although other percentages can be used. If median signal $ST_r(n)$ are computed, then the area based repolarization intervals are based on median signal $ST_r(n)$, instead of on the individual segments $ST_k(n)$. By way of example, six area based repolarization intervals are superimposed as shown in FIG. 6A and their cumulative repolarization curves are shown in FIG. 6B.

In step 40, the quantification system 12 determines if there are any more ECG signals to process. If there are more ECG signals to process, then the Yes branch is taken back to step 30. If there are no more ECG signals to process, then the No branch is taken back to step 42.

In step 42, the quantified area based repolarization interval or intervals are calculated. The calculated interval or intervals may be output or displayed in a variety of different formats, such as on an hourly basis, a day/night basis, or on a twenty-four hour basis.

The quantified area based repolarization interval or intervals may also be analyzed by quantification system 12 to detect any alterations in ventricular repolarization. In this particular embodiment, the morphology of the ventricular repolarization segment is analyzed by looking at the length of the interval needed to reach a certain percentage of A(n). For example, if the time need to reach a certain percentage deviates from a designated standard by more than a standard deviation, then the ventricular repolarization is designated as altered.

The quantified area based repolarization intervals allow for the identification of slow trends in the area based repolarization interval. For example, in the study of pharmacological agents, the morphology of the area based repolarization interval before, during and/or after exposure to the pharmacological agent can be examined to identify trends and problems.

Quantification system 12 may perform other types of analysis, such as repolarization duration vs. cycle length relationship—paired RTx % and RR intervals are determined, the RTx %/RR) slope and its 95% confidence interval are obtained and the scattergram of the raw RTx % vs. RR relationship is graphically displayed. The slope of the regression line is a measure of QT dynamicity.

Quantification system 12 may compare RTx % by RR interval bins to determine if there has been a change in the RTx % interval with an intervention that also may have a small effect on the heart rate, the RTx % interval is grouped into selected RR interval ranges, thus avoiding the need to correct for heart rate. One example of this approach is shown in the table in FIG. 7. In this table in FIG. 7, RTx %b refers to the RT interval during the baseline ECG recording and RTx %d refers to the RT value after drug administration. A statistical comparison of the difference between the RTx %b and RTx %d for values in the RR interval bin, such as the 601 to 700 msec RR interval range is represented by the P-value. Similar comparisons are provided for other RR interval bins, such as 701-800 msec and 801-900 msec as shown in FIG. 7, with RTx % values represented by X1 to X4. RR interval bins can be arbitrarily selected by the operator of the quantification system 12.

Referring to FIGS. 8A-24B, the output form the analysis of one patient with the present invention is illustrated. Referring back to FIG. 4, this embodiment of the method ends in step 44.

The present invention described above uses the principle of signal integration of the ventricular repolarization segment to accurately identify ventricular repolarization changes induced by physiologic conditions, such as exercise, cardiac disorders, such as heart disease, or pharmacological agents, such as the evaluation of the effect of a drug on the ventricular repolarization of the heart. The present invention can be applied to ECG signals acquired in variety of dynamic settings including: short- and long-term Holter monitoring, exercise ECG testing, bedside telemetry ECG monitoring, ECG recording using event recorders, implantable devices, or intracardiac electrodes.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefor, is not intended to limit the claimed processes to any order except as may be specified in the claims. Accordingly, the invention is limited only by the following claims and equivalents thereto.

What is claimed is:

1. A method for analyzing an effect of a pharmacological agent on an electrocardiogram (ECG) signal, comprising:

obtaining a first ECG signal having at least one beat, the beat having a first repolarization interval represented by a portion of the first ECG signal from a first T-wave starting point to a first T-wave ending point;

quantifying an area under the first ECG signal during the first repolarization interval;

quantifying a first time to reach at least one percentage of the area under the first ECG signal during the first repolarization interval;

administering the pharmacological agent;

after administering the pharmacological agent, obtaining a second ECG signal having at least one beat, the beat having a second repolarization interval represented by a portion of the second ECG signal from a second T-wave starting point to a second T-wave ending point;

quantifying an area under the second ECG signal during the second repolarization interval;

quantifying a second time to reach the at least one percentage of the area under the second ECG signal during the second repolarization interval;

detecting an altered ventricular repolarization based on the quantified first and second times.

2. The method of claim 1, wherein:
the first T-wave starting point comprises a point during the at least one beat of the first ECG signal at a first time after a first R peak location of the first ECG signal; and
the second T-wave starting point comprises a point during the at least one beat of the second ECG signal at a second time after a second R peak location of the second ECG signal.

3. The method of claim 2, wherein the first time after the first R peak location is approximately equal to the second time after the second R peak location.

4. The method of claim 2, wherein the first time after the first R peak location is approximately equal to 100 msec.

5. The method of claim 2, wherein the first time after the first R peak location is selected to avoid QRS complex components.

6. The method of claim 1, wherein:
the first T-wave ending point comprises a point during the at least one beat of the first ECG signal where a slope of the first repolarization interval is equal to or passes below a first threshold; and
the second T-wave ending point comprises a point during the at least one beat of the second ECG signal where a slope of the second repolarization interval is equal to or passes below a second threshold.

7. The method of claim 6, wherein the first threshold is substantially equal to the second threshold.

8. The method of claim 1, wherein:
the area under the first repolarization interval comprises a total area under the first repolarization interval; and
the area under the second repolarization interval comprises a total area under the second repolarization interval.

9. The method of claim 1, wherein at least one of the area under the first repolarization interval and the area under the second repolarization interval are determined using integration.

10. The method of claim 1, wherein:
the first repolarization interval is associated with a first RR-interval and a first R-peak of the first ECG signal;
the second repolarization interval is associated with a second RR-interval and a second R-peak of the second ECG signal;
the first T-wave ending point is determined as a distance from the R-peak of the first ECG signal equal to a fraction of the first RR-interval; and
the second T-wave ending point is determined as a distance from the R-peak of the second ECG signal equal to a fraction of the second RR-interval.

11. The method of claim 10, wherein:
the fraction of the first RR-interval is approximately 4/7 of the first RR-interval; and
the fraction of the second RR-interval is approximately 4/7 of the second RR-interval.

12. The method of claim 1, wherein the first ECG signal and the second ECG signal are obtained consecutively as one continuous ECG signal which may be split or indexed into the first ECG signal and the second ECG signal using a knowledge of when the pharmacological agent was administered during the continuous ECG signal.

13. The method of claim 1, further comprising filtering the first ECG signal and the second ECG signal.

14. The method of claim 13, wherein filtering the first ECG signal and the second ECG signal comprises low-pass filtering the first ECG signal and the second ECG signal.

15. The method of claim 13, wherein the filtering substantially preserves an initial shape of the first repolarization interval and substantially preserves an initial shape of the second repolarization interval.

16. The method of claim 13, wherein filtering the first ECG signal and the second ECG signal comprises:
filtering the first and second ECG signals in a forward direction through a filter; and
reversing the filtered first and second ECG signals, and running them back through the filter.

17. The method of claim 13, wherein filtering the first ECG signal and the second ECG signal comprises using a Butterworth filter and a bidirectional filtering technique.

18. The method of claim 1, further comprising:
cutting the first ECG signal into a first sequence of consecutive beats; and
cutting the second ECG signal into a second sequence of consecutive beats.

19. The method of claim 18, further comprising:
excluding non-normal beats from the first sequence of consecutive beats; and
excluding non-normal beats from the second sequence of consecutive beats.

20. The method of claim 18, further comprising:
removing one or more beats from the beginning of the first sequence of consecutive beats; and
removing one or more beats from the beginning of the second sequence of consecutive beats.

21. The method of claim 18, further comprising:
removing one or more beats from the end of the first sequence of consecutive beats; and
removing one or more beats from the end of the second sequence of consecutive beats.

22. The method of claim 18, further comprising:
determining a median beat, from the first sequence of consecutive beats, which will comprise the first repolarization interval; and
determining a median beat from the second sequence of consecutive beats, which will comprise a second repolarization interval.

23. The method of claim 1, further comprising removing a baseline from the first and second ECG signals.

24. The method of claim 23, wherein removing the baseline from the first and second ECG signals comprises using a Cubic-Spline interpolation of the baseline of the first and second ECG signals.

25. The method of claim 1, further comprising removing respiratory components from the first and second ECG signals.

26. The method of claim 1, wherein the second ECG signal corresponds to a period when the administered pharmacological agent is in effect.

27. The method of claim 1, wherein the second ECG signal corresponds to a period when the administered pharmacological agent is no longer in effect.

28. The method of claim 1, wherein detecting an altered ventricular repolarization based on the quantified first and second times comprises comparing the quantified first and second times.

29. The method of claim 28, wherein comparing the comparing the quantified first and second times comprises determining if the difference between the first and second times exceeds a designated standard.

30. A computer readable medium having stored thereon instructions for analyzing an effect of a pharmacological agent on an electrocardiogram (ECG) signal which, when executed by a processor, causes the processor to perform the following steps:
    obtaining a first ECG signal having at least one beat, the beat having a first repolarization interval represented by a portion of the first ECG signal from a first T-wave starting point to a first T-wave ending point;
    quantifying an area under the first ECG signal during the first repolarization interval;
    quantifying a first time to reach at least one percentage of the area under the first ECG signal during the first repolarization interval;
    administering the pharmacological agent;
    after administering the pharmacological agent, obtaining a second ECG signal having at least one beat, the beat having a second repolarization interval represented by a portion of the second ECG signal from a second T-wave starting point to a second T-wave ending point;
    quantifying an area under the second ECG signal during the second repolarization interval;
    quantifying a second time to reach the at least one percentage of the area under the second ECG signal during the second repolarization interval;
    detecting an altered ventricular repolarization based on the quantified first and second times.

31. A method for analyzing an effect of a pharmacological agent on an electrocardiogram (ECG) signal comprising a plurality of beat signals, each beat signal having a repolarization interval represented by a portion of the beat signal from a T-wave starting point to a T-wave ending point, the method comprising:
    administering the pharmacological agent at some point before, between, or during collection of the ECG signal;
    quantifying an area under each of selected beat signals during each respective repolarization interval; and
    quantifying a time to reach at least one percentage of the area under each of the selected beat signals during each respective repolarization interval.

32. The method of claim 31, further comprising: outputting the quantified times to reach the at least one percentage of the area under each of the selected beat signals during each respective repolarization interval versus time passed to enable analysis of the effect of the pharmacological agent over the time passed.

33. The method of claim 31, further comprising:
    determining a cycle length of each selected beat signal for which the time to reach the at least one percentage of the area under the selected beat signal, during the respective repolarization interval, is quantified;
    outputting the cycle lengths versus their corresponding times reach the at least one percentage of the area under the selected beat signal to enable analysis of the effect of the pharmacological agent.

34. The method of claim 33, further comprising:
    determining a regression line which corresponds the output data, whereby a slope of the regression line is a measure of the dynamicity of a QT dynamicity.

35. The method of claim 31, further comprising:
    grouping the quantified times to reach the at least one percentage of the area under each of the selected beat signals during each respective repolarization interval into bins; and
    outputting a statistical comparison of the quantified times to reach the at least one percentage of the area under each of the selected beat signals during each respective repolarization interval based on each interval bin.

36. The method of claim 35, wherein at least one of the interval bins comprises a pre-pharmacological agent administration time period.

37. The method of claim 35, wherein at least one of the interval bins comprises a post-pharmacological agent administration time period.

38. A system for analyzing an effect of a pharmacological agent on an electrocardiogram (ECG) signal, comprising:
    a) an ECG device;
    b) a storage device; and
    c) a quantification system configured to:
        1) be coupled to the ECG device and/or the storage device for obtaining the ECG signal;
        2) identify a first repolarization interval represented by a first portion of the ECG signal from a first T-wave starting point to a first T-wave ending point;
        3) quantify an area under the first ECG signal during the first repolarization interval;
        4) quantify a first time to reach at least one percentage of the area under the first ECG signal during the first repolarization interval;
        5) identify a second repolarization interval represented by a second portion of the ECG signal from a second T-wave starting point to a second T-wave ending point;
        6) quantify an area under the second ECG signal during the second repolarization interval;
        7) quantify a second time to reach the at least one percentage of the area under the second ECG signal during the second repolarization interval;
        8) detect an altered ventricular repolarization based on the quantified first and second times.

39. A method for analyzing an effect of a pharmacological agent on an electrocardiogram (ECG) signal, comprising:
    a) obtaining a first ECG signal having at least one beat, the beat having a first repolarization interval represented by a portion of the first ECG signal from a first T-wave starting point to a first T-wave ending point;
    b) filtering the first ECG signal;
    c) removing a first baseline from the first ECG signal;
    d) quantifying an area under the first ECG signal during the first repolarization interval;
    e) quantifying a first time to reach at least one percentage of the area under the first ECG signal during the first repolarization interval;
    f) administering the pharmacological agent;
    g) after administering the pharmacological agent, obtaining a second ECG signal having at least one beat, the beat having a second repolarization interval represented by a portion of the second ECG signal from a second T-wave starting point to a second T-wave ending point;
    h) filtering the second ECG signal;
    i) removing a second baseline from the second ECG signal;
    j) quantifying an area under the second ECG signal during the second repolarization interval;
    k) identifying a second time to reach the at least one percentage of the area under the second ECG signal during the second repolarization interval;

l) detecting an altered ventricular repolarization based on the quantified first and second times; and m) wherein:
1) the first T-wave starting point comprises a point during the at least one beat of the first ECG signal at a first time after a first R peak location of the first ECG signal;
2) the second T-wave starting point comprises a point during the at least one beat of the second ECG signal at a second time after a second R peak location of the second ECG signal;
3) the first time after the first R peak location is selected to avoid QRS complex components;
4) the second time after the second R peak location is approximately equal to the first time after the first R peak location;
5) the first T-wave ending point comprises a point during the at least one beat of the first ECG signal where a slope of the first repolarization interval is equal to or passes below a first threshold;
6) the second T-wave ending point comprises a point during the at least one beat of the second ECG signal where a slope of the second repolarization interval is equal to or passes below a second threshold;
7) the first threshold is substantially equal to the second threshold;
8) at least one of the total area under the first repolarization interval and the total area under the second repolarization interval are determined using integration;
9) filtering the first ECG signal and the second ECG signal comprises:
   i) filtering the first and second ECG signals in a forward direction through a filter;
   ii) reversing the filtered first and second ECG signals, and running them back through the filter; and
10) comparing the quantified first and second times comprises determining if the difference between the quantified first and second times exceeds a designated standard.

* * * * *